US005747256A

United States Patent [19]
Yan et al.

[11] Patent Number: 5,747,256
[45] Date of Patent: May 5, 1998

[54] HOMOGENEOUS DNA PROBE TITRATION ASSAY

[75] Inventors: Cheng F. Yan, Irvine; Fredrick S. Yein, Diamond Bar, both of Calif.

[73] Assignee: Beckman Instruments, Inc., Fullerton, Calif.

[21] Appl. No.: 579,039

[22] Filed: Dec. 19, 1995

[51] Int. Cl.⁶ .............................. C12Q 1/68; C12P 19/24
[52] U.S. Cl. .................................. 435/6; 435/91.2
[58] Field of Search .............................. 435/5, 6, 91.2; 935/77, 78

[56] References Cited

U.S. PATENT DOCUMENTS

| | | | |
|---|---|---|---|
| 4,045,384 | 8/1977 | Dorman | 260/8 |
| 4,275,149 | 6/1981 | Litman | 435/7 |
| 4,925,785 | 5/1990 | Wang et al. | 435/6 |
| 5,026,785 | 6/1991 | Mage | 525/329.4 |
| 5,306,615 | 4/1994 | Breillatt, Jr. | 435/6 |
| 5,306,619 | 4/1994 | Edwards | 435/6 |

FOREIGN PATENT DOCUMENTS

| | | |
|---|---|---|
| 0130523 | 1/1985 | European Pat. Off. . |
| 0152886 | 8/1985 | European Pat. Off. . |
| 0158443 | 10/1985 | European Pat. Off. . |
| 0 167 238 A | 1/1986 | European Pat. Off. . |
| WO 87 05334 A | 9/1987 | European Pat. Off. . |
| WO 90 02205 A | 3/1990 | European Pat. Off. . |
| WO 92 04469 A | 3/1992 | European Pat. Off. . |
| 8705334 | 9/1957 | WIPO . |
| 8504674 | 10/1985 | WIPO . |

OTHER PUBLICATIONS

Polsky–cynkin, R.; Clinical Chemistry: Use of DNA immobilized on plastic and Agarose Supports to Detect DNA by Sandwich Hybridization, pp. 1449 (vol. 31, No. 9).
Paul, W.E.; Fundamental Immunology: Hemagglutination and Hemaggultination Inhibition, 1984, pp. 638–640.

*Primary Examiner*—Eggerton A. Campbell
*Attorney, Agent, or Firm*—William H. May; Margaret A. Kivinski; Robbins & Berliner

[57] ABSTRACT

An assay for detecting the presence or amount of a target polynucleotide sequence of interest in a test sample is disclosed. The assay comprises the steps of forming a reaction mixture by combining in an assay medium (i) a first reagent and (ii) an aliquot of the test sample suspected of containing the target polynucleotide sequence. The reaction mixture is subjected to denaturing conditions, and exposed to hybridization conditions allowing the first reagent to hybridize with any target polynucleotide present. A second reagent is then added, the reaction mixture undergoes hybridization conditions and the change in turbidity of the reaction mixture is detected, correlating with the presence of the target polynucleotide in the sample.

24 Claims, 2 Drawing Sheets

(1) First Reagent:

Solid Particle     First Probe (2) Second Reagent:

Solid Particle     Second Probe (1) Combine First Reagent and buffer in a reaction cuvette.

(2) Isolate target double-stranded (ds) DNA from patient cells. Amplify the DNA if necessary, add to the reaction cuvette.

(3) Heat the mixture up to 90° C to denature target ds-DNA, then cool down to allow hybridization to occur.

(4) Add Second Reagent  to the cuvette and incubate under hybridization conditions.

(5) a. Negative reaction: Disease-specific target DNA is absent in the sample, then

Maximum aggregation & maximum light scattering are obtained b. Positive reaction: Disease-specific target DNA is present in the sample, then Particle aggregation is inhibited due to the presence of target DNA sequences in the patient sample

FIGURE 2

HOMOGENEOUS DNA PROBE TITRATION ASSAY

BACKGROUND

Diagnostic assays play a significant role in the detection and diagnosis of diseases. Of major impact has been the use of genetic analysis as a method for detecting genetic traits, abnormalities and diagnosis in clinical medicine. Recombinant nucleic acid techniques have revolutionized molecular biology and genetics by permitting the detection, isolation and characterization of specific deoxyribonucleic acid (DNA) fragments.

The development of genetic analysis has made possible the precise measurement of specific polynucleotides of interest in samples of serum, plasma, cerebral spinal fluid, amniotic fluid and urine. In particular, genetic analysis can be used to detect and identify etiological agents such as bacteria and viruses, to screen bacteria for antibiotic resistance, to aid in the diagnosis of genetic disorders such as Down's syndrome, sickle cell anemia and cystic fibrosis, and to detect cellular disorders such as cancerous cells.

Thus, the importance of genetic analysis makes this technique amenable to a wide variety of applications such as medical diagnostics, human genetics, prenatal diagnostics, forensic science and other disciplines of the biological sciences.

There are complications, however, with the use of genetic analysis as an assay. The sensitivity, accuracy, speed and versatility of these assays are often limited by the assay conditions. Such limitations can make detection and measurement of a specific polynucleotide sequence of interest unreliable which could cause inaccurate results leading to misdiagnosis and potentially inappropriate treatment.

There are a variety of known methods to detect specific polynucleotide sequences in a sample. Conventional methods for genetic analysis utilize state of the art hybridization assay techniques. Nucleic acid hybridizations can provide a very sensitive and specific approach to detecting and identifying nucleic acids in samples. Hybridization between particular base sequences or genes of interest in the sample nucleic acid generally involve immobilization of a sample nucleic acid on a solid support and adding labeled probe, or immobilization of the probe and labeling the sample nucleic acid insitu, or utilizing a dual hybridization technique requiring two probes, one which is immobilized and the other labeled.

There are disadvantages associated with these methods since the procedures required to accomplish immobilization are generally time consuming and generally require an additional step which can be undesirable for routine use in a clinical laboratory. Furthermore, these methods often require enzyme or radioactive tracer labeled nucleic acid probes.

Radioactively labeled nucleotide sequences are widely used, however, they can pose a risk to the user. Additionally, these radioactive materials have short half-lives and therefore have limited shelf lives.

Other methods include measuring the change of absorbance of a DNA solution, physically isolating hybridized DNA from non-hybridized DNA using chromatography or hydroxyapatite and quantitating the hybridized DNA. These methods also generally require a radioactive label.

For diagnostic applications in particular, the target polynucleotide sequence of interest may be only a small portion of a nucleic acid such as DNA or (ribonucleic acid) RNA in question, so that it can be difficult to detect their presence using nonisotopically labeled or end-labeled nucleotide probes. Much effort has been expended in increasing the sensitivity of the probe detection systems.

Therefore, while these genetic analysis procedures for detecting a particular polynucleotide sequence of interest can be useful, they are often disadvantageously time consuming, they can be harmful and these limitations can drastically reduce the potential sensitivity and accuracy of the assay.

At the present time, there exists a need for an assay for detecting the presence of a target nucleotide sequence in a sample in which the aforementioned problems are eliminated or substantially reduced. An assay is needed which has the sensitivity and specificity of nucleic acid hybridization techniques, yet does not require immobilization or the use of radioactive materials, is not time-consuming and is efficient, safe and effective. Further, it would be advantageous to have an assay which would be capable of detecting nucleic acid sequences at very low concentration.

SUMMARY OF THE INVENTION

The present invention is directed to an assay that meets these needs. The assay is used to determine the presence or amount of a target polynucleotide sequence of interest in a test sample. The assay comprises the steps of forming a reaction mixture by combining in an assay medium (i) a first reagent comprising a first probe bound to a solid particle and (ii) an aliquot of the test sample suspected of containing the target polynucleotide sequence. The first probe comprises a first single stranded nucleic acid fragment complementary to a first of two separated strands of a selected segment of the target polynucleotide sequence. The concentration of the target polynucleotide sequence of the test sample is in excess to the concentration of the first probe.

The reaction mixture is then subjected under denaturing conditions rendering the target polynucleotide sequence in the sample to be single stranded. The reaction mixture is then exposed under hybridization conditions to cause hybridization between the first probe and the first strand of the selected segment of the target polynucleotide sequence. In the presence of the target polynucleotide, substantially all of the first probe can be hybridized to the first strand of the selected segment of the polynucleotide sequence.

Next, a second reagent is added to the reaction mixture. The second reagent comprises a second probe bound to a solid particle. The second probe comprises a second single stranded nucleic acid fragment with the same nucleotide sequence as the second strand of the selected segment of the target polynucleotide. The second probe is complementary to the first probe. The first and second probes can be complementary to mutually exclusive portions of the target polynucleotide sequence.

The reaction mixture is incubated under hybridization conditions a sufficient time wherein the absence of the target polynucleotide, the first probe and the second probe can hybridize with each other and the reaction mixture becomes sufficiently turbid. In the presence of the target polynucleotide, the second probe can hybridize with the second single strand of the selected segment of the target polynucleotide. Hybridization of the first probe with the first strand of the selected segment of the target polynucleotide produces substantially no change in the turbidity of the reaction mixture. Combination of the second probe with the second strand of the selected segment of the target polynucleotide produces substantially no change in the turbidity of the reaction mixture.

The change in the turbidity of the reaction mixture can be detected and the presence or amount of the target polynucleotide can be determined.

The target polynucleotide can be a segment of DNA or RNA. The first probe and the second probe can be DNA or RNA fragments.

The target polynucleotide can have at least eight nucleotides. The selected segment of the target polynucleotide sequence can have at least four nucleotides.

The first probe and the second probe can have at least four nucleotides. These probes can be bound to the solid particle covalently or by adsorption. They can be bound to the solid particle directly or through a spacer molecule.

Preferably, the solid particles can be selected from the group consisting of polystyrene, charcoal, colloidal gold, bentonite, glass, silica gel, red blood cells, liposomes and latex. More preferably, the solid particles are latex.

The assay can be performed on test samples such as serum, plasma, saliva, cerebral spinal fluid, amniotic fluid, urine, feces, mucus, cell extracts, tissue extracts and pus.

The target polynucleotide sequence can be selected from the group consisting of Down's syndrome, Huntington's disease, sickle cell anemia, Lou Gehrig's diseases, cystic fibrosis, Tay-Sachs disease, multiple sclerosis, adult polycystic kidney disease, neurofibromatosis, beta-thalassemia, retinoblastoma, N. gonorrhoea, herpes simplex virus 1, herpes simplex virus II, *Brucella abortus, Bordetella pertussis, Shigella dysenteria, Haemophilus influenzae, Mycobacterium tuberculosis, Pseudomonas pseudomallei, Salmonella typhi, Salmonella typhimurium,* and *N. meningitidis.*

The target polynucleotide can be amplified prior to the step of combining.

DESCRIPTION OF THE DRAWINGS

These and other features, aspects, and advantages of the present invention will become better understood with reference to the following description, appended claims, and accompanying drawings where:

FIG. 2 is a schematic diagram outlining the steps of the homogeneous DNA probe titration assay to detect a polynucleotide sequence of interest.

DESCRIPTION

Figure 1:
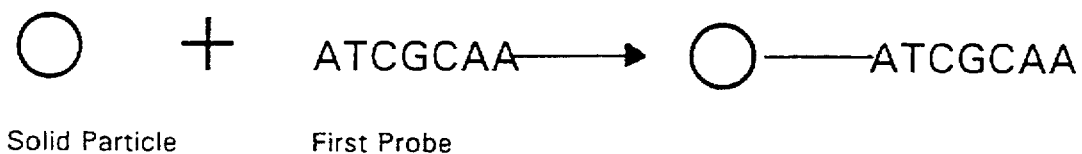
FIG. 1 is a schematic diagram outlining the steps of preparing the first and second reagents.
Figure 1:
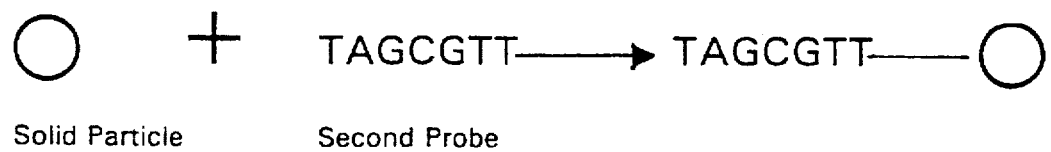

According to the present invention, there is provided a simple assay for detecting the presence or amount of a target polynucleotide sequence of interest in a test sample. Such an assay comprises the steps of forming a reaction mixture, subjecting the reaction mixture under denaturing conditions, exposing the reaction mixture under hybridization conditions, adding a second reagent to the reaction mixture, incubating the reaction mixture under hybridization conditions and determining the presence or amount of the target polynucleotide in the sample.

The use of nucleic acid hybridization as an analytical tool is based on the double stranded duplex structure of DNA. The hydrogen bonds between the purine and pyrimidine bases of the respective strands in double stranded DNA can be reversibly broken. The two complementary strands of DNA resulting from this melting or denaturation of DNA will associate (also referred to as reannealing or hybridization) to reform the duplexed structure. Contact of a first single stranded nucleic acid, either DNA or RNA, which comprises a base sequence sufficiently complementary to a second single stranded nucleic acid under appropriate conditions, will result in the formation of nucleic acid hybrids, as the case may be.

I. FORMING THE REACTION MIXTURE

The reaction mixture is formed by combining in an assay medium a first reagent and an aliquot of the test sample suspected of containing the target polynucleotide sequence of interest.

A. The First Reagent

The first reagent comprises a first probe bound to a solid particle.

1. The First Probe

The first probe comprises a first single stranded nucleic acid fragment complementary to a first of two separated strands of a selected segment of the target polynucleotide sequence. The nucleic acid fragments can be fragments from deoxyribonucleic acid (DNA) or ribonucleic acid (RNA) sequences. Preferably the nucleic acid fragment is single stranded. The nucleic acid fragments can be produced or obtained by any method known to those of ordinary skill in the art, e.g., synthetic production methods or enzymatic production methods, both in vitro and in vivo. DNA and RNA probes are single-stranded nucleic acid molecules generally synthesized by so-called gene machines or made using recombinant DNA methods.

The first probe is constructed so that the nucleotide base sequence of the probe match (and lend themselves to hybridization with) complementary nucleotide sequence of a first of two separated strands of a selected segment of the target polynucleotide sequence.

The first probe will comprise at least one single stranded base sequence substantially complementary to the target polynucleotide sequence to be detected. The first probe typically will exhibit detectable hybridization at one or more points with the target polynucleotide sequence of interest.

Preferably, the first probe is a nucleic acid fragment and will typically consist of chemically synthesized or biologically prepared DNA or RNA polynucleotides in the form of single-stranded sequences. If synthesized, the single-stranded DNA or RNA probe is fabricated so that its nucleic acid base sequence is complementary to a selected segment of the target polynucleotide sequence.

Typically, the probe fragment need not have perfect complementarity to the selected sequence to which it hybridizes. Hybridization can still be detected by suitable alteration of hybridization conditions such as buffer composition and hybridization temperature. Preferably, the probe nucleic acid fragment will be as complementary as possible to the selected segment of the target nucleotide sequence.

The nucleic acid fragment attached to the solid particle can be of almost any length, provided that the fragment is long enough to form a stable hybrid with the selected segment of the target polynucleotide sequence. The first probe nucleic acid fragment will typically have a minimum 4-base sequence, one base greater than an amino acid codon. Typically, five bases can form a stable hybrid duplex. Preferably, the first probe nucleic acid segment is from about 4 to about 20 nucleotides in length. The more nucleotides, the greater the specificity, however, this can create greater steric hindrance when the nucleic acid fragment is attached to the solid particle.

The short nucleic acid fragments are preferably produced by controlled digestion with DNAse I. Alternatively, sonication or digestion with other suitable nucleases can be used. Although the probes may have 10,000 bases or more, 5,000 is usually the maximum. The probe sequence preferably is substantially complementary to a sequence characteristic of the target polynucleotide of interest.

The RNA or DNA probe can be obtained in a variety of conventional manners. Typically, RNA can be isolated as the natural product of cells, such as 5s, 16s and 23s ribosomal RNAs from bacteria or cellular transfer RNAs. In vitro synthesis of RNA probes can also accomplished using state of the art techniques.

2. The Solid Particle

Choice of the solid particles depend on several factors which include: (1) hybridization conditions to be used, particularly temperature; (2) method to be used for covalent coupling to the single-stranded nucleic acid fragment; and (3) size of the single stranded nucleic acid fragment.

The choice of the solid particle can be governed by the effect of the rate of hybridization and binding of the probe to the target DNA. The solid particle preferably should provide sufficient sensitivity in order to detect the amount of target nucleotide sequence available for hybridization. Other considerations will be the ease of synthesis of the probe, the availability of instrumentation, the ability to automate, and convenience.

The particles employed in accordance with the methods of Cheng Yan, Chan S. Oh and Anthony Cheng in U.S. patent application Ser. No. 248,479, filed on May 23, 1994 and entitled "Reagents And Methods For The Rapid And Quantitative Assay Of Pharmacological Agents," herein incorporated by reference in its entirety, are macroscopic particles, preferably made of latex. The use of such macroscopic particles decreases the extent of complex formation needed to obtain a discernible change in light scatter or reflection. Thus, because of the presence of the macroscopic particles, target polynucleotide sequences that would otherwise be too small to detectable can be easily measured. The presence of the particles can affect the detection of the particular polynucleotide sequence using nephelometric or turbidimetric methods.

The size of the latex particle can depend on the length of the nucleic acid segment of the probe. Typically, the size of the latex particle can vary from about 40 nm to about 400 nm. Preferably the use of particles between about 80 nm to about 200 nm is preferred for DNA probes that measure targeted polynucleotide sequences by nephelometric or turbidimetric means. Such particles can be obtained from Seradyn, Inc., Indianapolis, Ind., U.S. Each 60 nm particle can contain on the average approximately 10,000 carboxyl groups and each 100 nm particle carries approximately 25,000 groups available for covalent coupling.

The solid particles can be any insoluble particle that is capable of attaching DNA or RNA covalently or by adsorption. The solid particle can be latex, charcoal, colloidal gold, bentonite, glass, silica gel, red blood cells or liposomes. Preferably, the solid particle is latex.

To produce fast rates of reaction, particles less than 0.1 μm can be used; to produce large changes of turbidity, core polymers are chosen with appropriate useful refractive indices.

3. Binding the First Probe to the Solid Particle

The nucleotide sequences can either be bound directly to the solid particle surface or can be attached through a spacer molecule which can be covalently bound or adsorbed to the solid particle surface.

Typically, nucleic acids have reactive amino functional groups as well as terminal phosphate groups and reactive hydroxyl groups in the sugar backbone. These reactive groups on the nucleic acid can be reacted with the reactive groups on latex or other particles to bind the DNA or RNA to the solid particle. Glass or other particles can be derivatized to form reactional functional groups. Nucleic acids can also be linked directly to polystyrene. The solid particle typically is spherical. It must be small enough to remain in suspension yet will generally have a large particle size relative to the molecular weight of the DNA or RNA probe (i.e. less than 500 microns).

Binding of the probe to the solid particle can be a covalent attachment or an adsorption. The nucleotide sequence can be directly covalently bound, the binding can occur randomly along the length of the DNA or RNA at the 5' end or the 3' end. The sequences can also be bound to the solid particle through a protein or other spacer linker.

For direct attachment of nucleic acids to the solid particle, this can be accomplished by the method in U.S. Pat. No. 4,045,384 by Dorman (herein incorporated by reference in its entirety). This procedure is based on forming an amide bond between latex and protein. There are three steps in the procedure. First, the carboxylated latex particle are activated by the formation of an ester at the latex surface through reaction with a water-soluble N-hydroxy compound (i.e. N-hydroxybenzotriazole or N-hydroxysuccinimide) and a water soluble carbodiimide (i.e. 1-cyclohexyl-3-[2-morpholinoethyl1]-carbodiimide methyl-p-toluene sulfonate (CMC). These materials are combined, stirred and cooled. As a result, an anhydride link is formed between the carboxyl group of the latex particle and the hydroxy nitrogen ($NOH_2$) group of the hydroxybenzotriazole. Next, the reaction mixture containing the hydroxybenzotriazole derivative attached is cleaned by dialysis to remove the unreacted reactants. Single stranded DNA or RNA can be covalently bonded to the activated latex particle by combining the latex-hydroxybenzotriazole complex with single stranded DNA or RNA and agitating the combination at room temperature. The product of this procedure has been shown to be single stranded DNA covalently attached to the latex particle at random along the length of the DNA. Similarly, this method can be used to covalently attach RNA.

Additionally, nucleic acids can be attached to solid particles by linker molecules which can be adsorbed or covalently bonded to latex. Nucleic acids can be covalently linked to polysaccharides by several different methods. Polysaccharides can be partially oxidized to yield reactive aldehyde groups which can in turn be reacted with particles having suitably reactive groups such as amino groups (i.e. amino functional latex).

Additionally, latex particles can be coupled to avidin, as described by Yan, C. et al. in patent application No. 248,479. In this method, the nucleotide sequence can be coupled to biotin (Chu et al., DNA, Vol. 4, pp. 327–331, 1985, herein incorporated by reference). Since avidin and biotin have a strong coupling constant, the latex particle can be bound to avidin, which can be bound to biotin attached to the nucleotide sequence of the probe. Typically, the synthesis of the biotinylated oligodeoxyribonucleotides can be the following reaction sequence. A DNA probe sequence complementary to the target nucleotide sequence can be converted to its 5' phosphate derivative and subsequently converted to the 5' ethylenediamine adduct via the 5' phosphorimidizolide intermediate. N-hydroxysuccinimidobiotin can be added and the biotinylated deoxyribonucleotide derivatives can be isolated and purified.

For covalent binding, carbodiimide coupling reaction has been used by those skilled in the field for the purpose of covalently linking DNA to solid supports such as agarose.

The latex solid particles can be chosen for high refractive indices which, together with particle size and detection wavelength, maximize the rate of turbidity change when the particle aggregates. In these cases, the shell polymer can contain epoxies and are chosen for its ability to covalently bind proteins, or a synthetic linker. For methods where protein linkers are preferred, the polynucleotide sequences can be covalently bound the solid particle by standard coupling procedures with either carbodiimide or glutaraldehyde.

B. The Test Sample

The test sample preferably contains the nucleic acid having the target polynucleotide sequence of interest. The test sample to be assayed can be any medium of interest, and will usually be a liquid sample of medical, veterinary, environmental, nutritional or industrial significance. Human and animal specimens and body fluids particularly can be assayed by the present method, including serum, plasma, saliva, cerebral spinal fluid, amniotic fluid, urine, feces, mucus, cell extracts, tissue extracts and pus. Additional test samples include milk, fecal matter, lung aspirates, throat swabs, genital swabs and exudates, rectal swabs, and nasopharyngal aspirates.

1. The Target Polynucleotide

The target polynucleotide sequence of interest can be any polynucleotide sequence present naturally in a sample. It can be in a material in or derived from a cellular system. It can be a subcellular component as a virus or viroid or virus like particle. It can be a deoxyribonucleic acid (DNA) sequence or a ribonucleic acid (RNA) sequence. It can be single stranded or double stranded. It can be derived from a pathogen. It can be a sequence of a prokaryote; a eukaryote, such as human, or a virus or an extra chromosomal genetic element. The target polynucleotide sequence of interest can be derived from all or any part of the genome.

The polynucleotide sequence can be any gene or polynucleotide sequence of interest (DNA or RNA). Any source of nucleic acid, in purified or nonpurified form, can be utilized as the starting nucleic acid or acids, provided it is suspected of containing the specific nucleic acid sequence desired. Thus, the process may employ, for example, DNA or RNA, including messenger RNA, which DNA or RNA may be single stranded or double standard. In addition, a DNA-RNA hybrid which contains one strand of each may be utilized.

It is only necessary that a sufficient number of bases of the sequence be known enough. The greater the knowledge about the bases of the sequences, the greater that can be specificity of the sequence of the target nucleotide sequence, and thus the greater the efficiency of the process.

The selected segment of the target polynucleotide sequence can be a portion of the entire target polynucleotide sequence where the base sequence is known. Typically, the selected segment of the target polynucleotide has at least four nucleotides. Preferably, the selected segment of the target polynucleotide sequence is at least eight polynucleotides.

Preferably, the target polynucleotide sequence is selected from the group consisting of Down's syndrome, Huntington's disease, sickle cell anemia, Lou Gehrig's disease, cystic fibrosis, Tay-Sachs disease, multiple sclerosis, adult polycystic kidney disease, neurofibromatosis, beta-thalassemia, retinoblastoma, N. gonorrhea, herpes simplex virus 1, herpes simplex virus II, *Brucella abortus*, *Bordetella pertussis*, *Shigella dysenteria*, *Pseudomonas pseudomallei*, *Salmonella typhi*, *Salmonella typhimurium*, and *N. meningitidis*.

Bacterial or viral DNA can be cleaved at selected sites on either side of the DNA fragment of interest. The DNA fragment can be isolated from other fragments and purified electrophoretically. The isolated DNA fragments can then be amplified by inserting them into a plasmid or a bacterial virus (bacteriophage), which is in turn inserted into an appropriate host cell. As the cells containing the plasmid proliferates, the plasmid also replicates, producing many copies of the DNA fragment to be used as the probe. Similarly, polymerase chain reaction method can be used to amplify the DNA fragment. After the cells have been allowed to proliferate, the hybrid plasmids are isolated and purified, resulting in many copies of the DNA fragment.

2. Amplification of the Target Polynucleotide Sequence in the Sample

Prior to the step of combining and prior to hybridization, the target polynucleotide can be amplified using any state of the art techniques for amplification. Preferably, the polymerase chain reaction (PCR techniques, well known to those with skill in the art) method is used. Amplification of the target polynucleotide can increase the sensitivity of the assay.

Amplification is useful when the amount of target polynucleotide available for analysis is very small, as for example, in the prenatal diagnosis of sickle cell anemia using DNA from fetal cells. Amplification is particularly useful if such an analysis is to be done on a small sample using non-radioactive detection techniques which may be inherently insensitive.

In cases where a relatively small number of pathogenic organisms are present in a clinical sample from an infected patient, the DNA extracted from the samples of these patients may constitute only a very small fraction of the total DNA in the sample. Specific amplification of suspected target sequences prior to hybridization detection of the DNA samples could improve the sensitivity and specificity of these procedures.

The amount of target polynucleotide can be determined through amplification conditions, and the concentration of the test sample is preferably in excess to the concentration of the first reagent to ensure maximum efficiency during hybridization.

C. The Assay Medium

The assay medium includes the first reagent and an aliquot of the test sample and can further include a buffer.

The assay medium can further include a buffer with pH between about 6.5 to about 8. Preferably, the pH buffer of the reaction mixture is between about 7 to about 7.5 allowing the amine groups of the nucleic acids to be protonated allowing for maximum hydrogen bonding between base pairs of complementary strands.

The buffer can further include additional components. Preferably, detergents are included in the buffer to keep the particles from self-associating. Typically, the concentration of the detergents is greater than about 2%. The detergents can be any non-ionic detergent, such as alkylpolyoxyethylene, alkyphenylpolyoxyethylene ether (especially Triton-X™) and acylpolyoxyethylene sorbitan ester (especially Tween-20™).

Additionally, polymers can be included in the buffer to change the water density which allows the solid particles to keep afloat for maximum hybridization conditions. Polyethylene glycol is preferably the polymer.

D. The Amounts of the First Reagent and Test Sample

The amounts of the test sample utilized in the reaction mixture will vary widely, depending on the nature of the solid particle and the stringency of the hybridization Preferably, substantial excess over a stoichiometric amount of the known target polynucleotide sequence to be hybridized relative to the amount of the probe will be employed to enhance the rate of hybridization and to allow the quantifying of the amount of target polynucleotide sequence present. For example, a 100 fold excess of the select target polynucleotide sequence to probe will allow rapid hybridization of all probe.

II. SUBJECTING THE REACTION MIXTURE UNDER DENATURING CONDITIONS

Where the test sample obtained from the patient or other source to be tested contains principally double stranded nucleic acids, such as contained in cells, the test sample can be treated to denature the nucleic acids, rendering the target polynucleotide sequence of interest single stranded.

Denaturing of the target polynucleotide sequence of interest can be accomplished by alkali treatment (e.g., 0.1N sodium hydroxide). Preferably, the denaturing conditions are accomplished by heating. At least a portion of the genetic material of the sample being in single strands form, but preferably all of the target polynucleotides in the sample is in single strand form. Typically, at least a portion of the genetic material of polynucleotide sequence are rendered in single strand form. However, it is highly preferred that the target polynucleotide sequence be in substantially single stranded form because polynucleotide sequence in duplex form generally do not participate in hybridization.

If necessary, prior to the denaturing step, the test sample can be subjected to conditions to release the nucleic acid from the cells. Release of the nucleic acids can be accomplished by mechanical disruption (freeze/thaw, abrasion, sonication), physical/chemical disruption (detergents such as polyoxyethylene ether detergents under the Triton™ trademark, polyoxytheylenesorbitan detergents known as Tween, sodium dodecylsulfate, alkali treatment, osmotic shock or heat), or enzymatic lysis. The resulting reaction mixture will contain nucleic acids in single stranded form which can then be assayed according to the present hybridization method.

If the nucleic acid contains two strands, it is necessary to separate the strands of the nucleic acid before it can be used as a template to hybridize with the probes, either as a separate step or simultaneously. This strand separation can be accomplished by any suitable denaturing method including physical, chemical or enzymatic means. One physical method of separating the strands of the nucleic acid involves heating the nucleic acid until it is completely (>99%) denatured. Typical heat denaturation may involve temperatures ranging from about 800° C. to 105° C. for times ranging from about 1 to 10 minutes. Strand separation can also be induced by an enzyme from the class of enzymes known as helicases or the enzyme RecA, which has helicase activity and in the presence of riboATP is known to denature DNA.

III. EXPOSING THE REACTION MIXTURE TO HYBRIDIZATION CONDITIONS

The reaction mixture is exposed under hybridization conditions to cause hybridization between the first probe and the first strand of the selected segment of the target polynucleotide sequence, whereby in the presence of the target polynucleotide, substantially all of the first probe will be hybridized to the first strand of the selected segment of the target polynucleotide sequence.

As used herein, the term "hybridization conditions" means those conditions which enable the first probe to form stable probe-target hybrids. Various hybridization conditions can be employed in the assay. The proper hybridization conditions can be determined by the length of the probes, and the guanosine plus cytosine content of the probes or the target polynucleotide.

During hybridization, the single-stranded target polynucleotide sequence derived from the test sample is reacted with the first probe under conditions where hybridization of the first probe with the target polynucleotide can occur.

The particular hybridization technique employed is not a critical element of the present invention. Various hybridization solutions can be employed, comprising from about 20 to 60, preferably 40 to 50, volume percent of an inert polar organic solvent. A common hybridization solution can employ about 50 percent formamide, about 0.05 to 0.5M sodium phosphate, and minor amounts of EDTA. Alternatively, aqueous solutions containing these salts and free of organic solvents such as formamide can be employed. The hybridization time employed can be one-half hour or less, and up to several hours or more as desired.

The extent of hybridization is affected by various factors, including temperature, probe concentration, probe length, ionic strength, time and the like. As an illustrative example, the extent of hybridization can be varied by changing the polarity of the reactant solution by manipulating the concentration of formamide in the range of about 0 to 50 percent. Alternatively, temperatures can be varied in the range of about 20° C. to 85° C., usually 30° C. to 75° C.

Hybridization conditions directed toward avoidance of nonspecific binding are preferred.

Typically, hybridization will proceed at slightly elevated temperatures, from between about 35° C. and 90° C. Preferably, the temperature is about 90° C.

The degree of complementarity between the target polynucleotide sequence of interest and the first reagent probe strands required for hybridization to occur depends on the stringency of the conditions. The extent and specificity of hybridization can be affected by the following principal conditions:

(1) The purity of the nucleic acid preparation.

(2) The base composition of the probe-G-C base pairs will exhibit greater thermal stability than A-T or A-U base pairs. Thus, hybridizations involving higher GC-content will be stable at higher temperatures.

(3) The length of homologous base sequence—Any short sequence of bases (e.g., less than 4 bases), has a high degree of probability of being present in many nucleic acids. Thus, little or no specificity can be attained in hybridizations involving short sequences. The present homologous probe sequence is typically at least four nucleotides, usually 20 bases or more and preferably between 20 to 30 bases. The homologous probe sequence can often be between 300–1000 nucleotides.

(4) Ionic strength—The rate of reannealing increases as the ionic strength of the reaction mixture increases. Thermal stability of the hybrids also increases.

(5) Nucleic acid concentration and incubation time— Preferably, according to the present invention, the target polynucleotide in the test sample is in excess to the first and second probes.

(6) Denaturing reagents—The presence of hydrogen bond disrupting reagents such as formamide and urea increases the stringency of hybridization.

IV. ADDING TO THE REACTION MIXTURE A SECOND REAGENT

After the reaction mixture is exposed under hybridization conditions with the first reagent, a second reagent is added to the reaction mixture.

The second reagent comprises a second probe bound to a solid particle. The second probe comprises a second single stranded nucleic acid fragment with the same nucleotide sequence as the second strand of the selected segment of the target polynucleotide sequence, whereby the second probe is complementary to the first probe, and the first and second probes are complementary to mutually exclusive portions of the target polynucleotide sequence.

The second probe triggers the reaction mixture by titrating unhybridized first reagent probe and unhybridized target polynucleotide.

As used herein, the term "mutually exclusive" means that during hybridization by the first and second probe fragments with each target polynucleotide sequence, the two probes should not compete for the same nucleotide base sequence on the target polynucleotide to the extent that hybridization is prevented.

The second probe nucleic acid segment has been described in detail under the heading of the first probe; the only difference being that the second probe is complementary to the first probe.

The solid particle is identical to the solid particle previously described herein.

V. INCUBATING THE REACTION MIXTURE UNDER HYBRIDIZATION CONDITIONS

After addition of the second reagent, the reaction mixture is incubated under hybridization conditions a sufficient time. Hybridization conditions have been previously described in detail.

In the absence of the target polynucleotide, the first probe and the second probe can hybridize with each other allowing the reaction mixture to become sufficiently turbid due to the agglutination of the solid particles attached to each probe.

In the presence of the target polynucleotide, the second probe can hybridize with the second single strand of the selected segment of the target polynucleotide since the first probe has already been hybridized to the first single strand of the selected segment of the target polynucleotide sequence.

Hybridization of the first probe with the first strand of the selected segment of the target polynucleotide sequence can produce substantially no change in the turbidity of the reaction mixture. Combination of the second probe with the second strand of the selected segment of the target polynucleotide can also produce substantially no change in the turbidity of the reaction mixture.

Turbidity results when there is maximum aggregation of the solid particles which can result in maximum light scattering. When the target polynucleotide sequence is present in the reaction mixture, particle aggregation can be inhibited. The extent of interference with particle agglutination is directly related to the amount of complementary nucleic acids in the sample. If there are only a few complementary sequences in the sample, particle agglutination will be interfered with to a lesser extent than if the sample contains a large number of sequences complementary to sequences on the latex particles.

If the reaction mixture contains target polynucleotide sequences which are complementary to those attached to the solid particle, hybridization will occur and there will be no particle agglutination. If there are no complementary strands to the probe, then hybridization of the probes will occur and the presence of particle agglutination can be detected.

This is because the first probe in the reaction mixture has already hybridized to one strand of the target polynucleotide sequence of interest and the second probe can only hybridize to the complementary single stranded portion of the unhybridized section of the target polynucleotide sequence.

VI. DETECTING THE CHANGE OF THE REACTION MIXTURE

Typically, after hybridization conditions, the detection step requires a separation step which separates that part of the composition which has hybridized to the sample being examined from that part which has not. Such separation can be carried out by a washing step.

According to the present invention, after the hybridization step is completed, a separation step is not necessary in the detection process.

Preferably, the solid particles used as the first and second reagents are latex. Latex aggregation can lead to detectable increase in light scatter or light absorbance allowing sensitive detection. Latex particles containing complementary strands of nucleic acid will aggregate and complementary nucleic acid that is free in the assay medium will inhibit the aggregation of the latex particles coated with the complementary nucleic acid fragments.

Agglutination of the particles will be inhibited or prevented and its absence will indicate that the target polynucleotide sequence of interest is present in the test sample. Hence, the presence of the target polynucleotide is related (proportional or correlates) to the amount of turbidity in the reaction mixture.

To automate these turbidimetric assays for current clinical analyzers, one must have particles that yield a high change of turbidity upon aggregation and produce fast reaction rates reproducibly over long periods of storage.

In the detecting step, the detection of agglutination can be carried out visually. Preferably, the degree of agglutination is measured by turbidimetric, or nephelometric methods, and is indicative of the extent of hybridization of the target nucleotide sequence. This can be proportional to the presence of the nucleotide sequence in the test sample. Particle counting techniques to detect agglutination can also be used.

It is possible to detect nucleotide sequence of interest in a test sample. An important characteristic is that the reactants are not immobilized. The reactants are either in solution or suspended to allow hybridization to occur. This permits for more efficient and rapid hybridization to detect the nucleotide sequence of interest. Additionally, this is a homogeneous assay. That is, no separation of bound and unbound phases is required in order to detect the nucleotide sequence of interest. This method is highly specific since the probe will only hybridize to the nucleotide sequence which is complementary to that probe.

A response curve can be created using samples with increasing amounts of target polynucleotide. The degree of inhibition can be indicative of the presence and concentration of the target polynucleotide in the test sample.

In the interest of clarity, the following example is intended to illustrate, but in no way limit the scope of, the present invention.

EXAMPLE (Prospective)

PREPARATION OF FIRST AND SECOND REAGENTS

Referring now to FIG. 1, there is illustrated a schematic diagram outlining the steps of preparing the first and second reagents.

1. The Solid Particles a. Activation Of Carboxylated Latex

Carboxylated latex (Seradyn, Inc., Indianapolis, Ind.) used as the solid support in covalent binding with DNA or RNA is prepared according to the method described by Dorman in U.S. Pat. No. 4,045,384 (herein incorporated by reference in its entirety). Activation of the carboxyl groups results from the reaction of the carboxylate latex with N-1-hydroxybenzotriazole in the presence of 1-cyclohexyl-3-[2-morpholinoethyl1]-carbodiimide methyl-p-toluene sulfonate (CMC).

0.2 ml of N-1-hydroxybenzotriazole solution which is prepared by dissolving 100 mg of N-1-hydroxybenzotriazole (Aldrich Chemical Co., Inc., Milwaukee, Wis.) in 1.7 ml dimethylformamide (DMF) and 2.6 ml water is added to 1 ml of carboxylate latex (0.1 micron in diameter, 2.5% solids). The resulting solution is placed in a cold room (4° C.) and 0.1 ml of CMC (50 mg/ml in water at 0° C.) is added dropwise. The mixture is mixed in the cold room for four hours. The resulting mixture is then dialyzed against 0.1M NaCl to remove the side products and unreacted materials.

2. Covalent Bonding Of DNA To The Modified Latex Solid Particles.

The first probe poly(dA)$_9$, or the second probe poly(dT)$_9$, is added while the modified latex is being stirred in a cold room. The pH of the mixture (6.8) is raised to 7.2 by the addition of 0.5M dibasic sodium phosphate. The mixture is allowed to stir for 5 days in the cold room. The latex particles are next spun down and washed with 0.1% SDS solution. The spinning and washing procedures are repeated two more times.

The first reagent: single stranded poly(dA)$_9$, attached on the microparticle (100 micron in size), is resuspended in a solution of 0.15 NaCl, 0.2% Tween-20™, 0.1% polyvinylpyrrolidone, and 0.015 sodium acetate buffer, pH 7.0. This first reagent solution is adjusted to contain about 0.025 ug probe/5 mL.

The second reagent: single stranded poly(dT)$_9$, attached on the microparticle (100 micron in size), is resuspended in solution of 0.15 NaCl, 0.2% Tween-20™, 0.1 polyvinylpyrrolidone, 0.015 sodium acetate buffer, pH 7.0. This second reagent solution is adjusted to contain about 0.25 ug probe/5 mL.

THE ASSAY FORMAT

Referring now to FIG. 2, there is illustrated a schematic diagram outlining the steps of the homogeneous DNA probe titration assay to detect a polynucleotide sequence of interest.

(1) A target DNA sequence of interest solution is prepared by dissolving 0.5 mg of double stranded poly(dA:dT) in 10 mL of 0.015M sodium citrate buffer, pH 7.0. This solution should have an absorbance at 260 nm of approximately 1.0. This target DNA solution is serially diluted with 0.015 M sodium citrate buffer, pH 7.0 to produce two target DNA samples in concentration of 0.5 ug/mL and 1.0 ug/mL.

(2) An aliquot of 0.5 mL of each target DNA of the test sample is pipetted into a tube. Two sets of samples are made and each set contains one replicate sample at each concentration.

(3) One set of tubes is incubated at 80° C. for 30 minutes to denature the double stranded target DNA sequence for hybridization, while the other set is incubated at 30° C. as a double stranded DNA control. The third set of tubes containing only 0.015M sodium citrate buffer is incubated at 80° C. for 30 minutes to serve as negative control.

(4) First probe hybridization: At the end of incubation period, 4.5 mL of the first reagent solution is added to each tube. Immediately, the tubes are cooled down to 30° C. and incubated for 20 minutes.

(5) Following the first probe hybridization, 0.1 mL of the second reagent solution is added to each tube and incubated at 30° C. for another 20 minutes to titrate the unhybridized first reagent probe.

(6) Absorbance at 600 nm of the reaction mixture in each tube is measured against sodium citrate buffer blank in a spectrophotometer.

3. Results:

In the absence of target DNA, the first probe and second probe can hybridize with each other, resulting in the reaction mixture being sufficiently turbid.

In the presence of denatured target DNA, the first probe can hybridize to a first strand of target DNA and the second probe can hybridize with the second single strand of the target polynucleotide producing a change in turbidity.

(1) Negative Control: $A_{600nm}$=0.358. Because all the first probes cannot hybridize with the target DNA sequence which is absent from this solution (negative control), and therefore are available for being titrated or hybridized with the second probe. Hybridization between the first and second probes results in a hybridized particles larger than 200 micron in size, shown by the increase in absorbance at 600 nm.

(2) Target DNA Samples: The $A_{600nm}$=0.029 for 0.5 ug/mL DNA sample and $A_{600nm}$=0.001 for 1.0 ug/mL DNA sample. When the first probes partially hybridize with the denatured target DNA as in the 0.5 ug/mL sample, only a little part of unhybridized left to be titrated by the second probe, resulting in the drastic decrease in absorbance to 0.029. As in the case for high concentration DNA sample at 1 ug/mL, all the first probes can hybridize with the target DNA and in the reaction mixture no first probe is left to be titrated by the second probes. This results in a zero absorbance reading.

(2) Double Strand DNA Control: $A_{600nm}$=0.355 for 0.5 ug/mL DNA sample and 0.362 for 1.0 ug/mL. The double stranded DNA can hybridize with the probe only after being denatured into single stranded DNA. Without high temperature heating, the DNA in these tubes remains double stranded and cannot hybridize with either first or second probe. Therefore, the absorbance for these two samples is as high as that of the Negative Controls.

The previously described present invention has many advantages. The advantages include having an assay which can detect a target polynucleotide sequence of interest in a test sample which has the specificity of nucleic acid hybridization techniques, can detect small amounts of polynucleotide and can be used with current automated instrumentation allowing less time to be consumed and greater efficiency. The stability and relative safety of the reagents used should make this assay especially valuable in routine medical diagnosis as well as in basic research.

Although the present invention has been described in considerable detail with reference to certain preferred versions, other version are possible. Thus, the spirit and scope of the appended claims should not be limited to the description of the preferred versions contained herein.

What is claimed is:

1. A method for detecting the presence or amount of a target polynucleotide sequence of interest in a test sample, comprising the steps of:
   a) forming a reaction mixture by combining in an assay medium:
      (i) a first reagent comprising a first probe bound to a solid particle, the first probe comprising a first single stranded nucleic acid fragment complementary to a first of two separated strands of a selected segment of the target polynucleotide sequence; and
      (ii) an aliquot of the test sample suspected of containing the target polynucleotide sequence;

wherein the concentration of the test sample is in excess to the concentration of the first probe;

b) subjecting the reaction mixture under denaturing conditions rendering the target polynucleotide sequence in the sample to be single stranded;

c) exposing the reaction mixture under hybridization conditions to cause hybridization between the first probe and the first strand of the selected segment of the target polynucleotide sequence;

whereby in the presence of the target polynucleotide, substantially all of the first probe will be hybridized to the first strand of the selected segment of the target polynucleotide sequence;

d) adding to the reaction mixture a second reagent, the second reagent comprising a second probe bound to a solid particle, the second probe comprising a second single stranded nucleic acid fragment with the same nucleotide sequence as the second strand of the selected segment of the target polynucleotide sequence, whereby the second probe is complementary to the first probe, and whereby the first and second probes are complementary to mutually exclusive portions of the target polynucleotide sequence;

e) incubating the reaction mixture under hybridization conditions a sufficient time;

wherein the absence of the target polynucleotide, the first probe and the second probe can hybridize with each other, whereby the reaction mixture becomes sufficiently turbid;

wherein the presence of the target polynucleotide, the second probe can hybridize with the second single strand of the selected segment of the target polynucleotide;

whereby the hybridization of the first probe with the first strand of the selected segment of the target polynucleotide produces substantially no change in the turbidity of the reaction mixture, and combination of the second probe with the second strand of the selected segment of the target polynucleotide produces substantially no change in the turbidity of the reaction mixture; and f) detecting the change in turbidity of the reaction mixture, wherein the change in turbidity correlates with the presence of the target polynucleotide in the sample.

2. The method of claim 1, wherein the target polynucleotide is a segment of DNA.

3. The method of claim 1 wherein the target polynucleotide is a segment of RNA.

4. The method of claim 1, wherein the first probe is a DNA or RNA fragment.

5. The method of claim 1, wherein the second probe is a DNA or RNA fragment.

6. The method of claim 1, wherein the target polynucleotide has at least eight polynucleotides.

7. The method of claim 1, wherein the selected segment of the target polynucleotide sequence has at least four nucleotides.

8. The method of claim 1, wherein the first probe has at least four nucleotides.

9. The method of claim 1, wherein the second probe has at least four nucleotides.

10. The method of claim 1, wherein the first and second probes are bound to the solid particle covalently or by adsorption.

11. The method of claim 1, wherein the first and second probes are bound to the solid particle directly or through a spacer molecule.

12. The method of claim 1, wherein the solid particles can be selected from the group consisting of polystyrene, charcoal, colloidal gold, bentonite, glass, silica gel, red blood cells, liposomes and latex.

13. The method of claim 12, wherein the solid particle is latex.

14. The method of claim 1, wherein the test sample is selected from the group consisting of serum, plasma, saliva, cerebral spinal fluid, amniotic fluid, urine, feces, mucus, cell extracts, tissue extracts and pus.

15. The method of claim 1, wherein the target polynucleotide sequence is selected from the group consisting of Down's syndrome, Huntington's disease, sickle cell anemia, Lou Gehrig's disease, cystic fibrosis, Tay-Sachs disease, multiple sclerosis, adult polycystic kidney disease, neurofibromatosis, beta-thalassemia, retinoblastoma, N. gonorrhoea, herpes simplex virus 1, herpes simplex virus II, *Brucella abortus, Bordetella pertussis, Shigella dysenteria, Haemophilus influenzae, Mycobacterium tuberculosis, Pseudomonas pseudomallei, Salmonella typhi, Salmonella typhimurium,* and *N. meningitidis.*

16. The method of claim 1, wherein the target polynucleotide is amplified prior to the step of combining.

17. The method of claim 1, wherein the step of detecting the turbidity can be measured by methods selected from the group consisting of the naked eye, turbidimetry, light scattering methods and nephelometry.

18. The method of claim 1, where in the assay medium further includes a buffer.

19. The method of claim 18, wherein the buffer has a pH from about 6.5 to about 8.

20. The method of claim 18, wherein the buffer includes a detergent selected from the group consisting of Triton X-100, and Tween-20™.

21. The method of claim 18, wherein the buffer further includes polyethylene glycol.

22. A method for detecting the presence or amount of a target polynucleotide sequence of interest in a test sample, the target polynucleotide sequence having at least eight polynucleotides, the method comprising the steps of:

a) forming a reaction mixture by combining in an assay medium:

(i) a first reagent comprising a first probe bound to a latex particle, the first probe comprising a first single stranded nucleic acid fragment having at least four nucleotides, the first probe complementary to a first of two separated strands of a selected segment of the target polynucleotide sequence, the selected segment having at least four nucleotides; and (ii) an aliquot of the test sample suspected of containing the target polynucleotide sequence;

wherein the concentration of the test sample is in excess to the concentration of the first probe;

b) subjecting the reaction mixture under denaturing conditions rendering the target polynucleotide sequence in the sample to be single stranded;

c) exposing the reaction mixture under hybridization conditions to cause hybridization between the first strand of the selected segment of the target polynucleotide sequence;

whereby in the presence of the target polynucleotide, substantially all of the first probe will be hybridized to the first strand of the selected segment of the target polynucleotide sequence;

d) adding to the reaction mixture a second reagent, the second reagent comprising a second probe bound to a latex particle, the second probe comprising a second single stranded nucleic acid fragment having at least four nucleotides, the second single stranded nucleic acid segment having the same nucleotide sequence as the second strand of the selected segment of the target polynucleotide sequence, whereby the second probe is complementary to the first probe, and whereby the first and second probes are complementary to mutually exclusive portions of the target polynucleotide sequence;

e) incubating the reaction mixture under hybridization conditions a sufficient time;

wherein the absence of the target polynucleotide, the first probe and the second probe can hybridize with each other, whereby the reaction mixture becomes sufficiently turbid;

wherein the presence of the target polynucleotide, the second probe can hybridize with the second single strand of the selected segment of the target polynucleotide;

whereby the hybridization of the first probe with the first strand of the selected portion of the target polynucleotide produces substantially no change in the turbidity of the reaction mixture, and combination of the second probe with the second strand of the selected segment of the target polynucleotide produces substantially no change in the turbidity of the reaction mixture; and f) detecting the change in turbidity of the reaction mixture, wherein the change in turbidity correlates with the presence of the target polynucleotide in the sample.

23. The method of claim 1, wherein the second probe triggers the reaction mixture by titrating unhybridized first reagent probe and unhybridized target polynucleotide.

24. The method of claim 22, wherein the second probe triggers the reaction mixture by titrating unhybridized first reagent probe and unhybridized target polynucleotide.

* * * * *